United States Patent [19]

Khanna et al.

[11] Patent Number: 5,536,830

[45] Date of Patent: Jul. 16, 1996

[54] PROCESS FOR P-NITROBENZYL ESTER CLEAVAGE IN CEPHALOSPORIN

[75] Inventors: Jag M. Khanna; Yatendra Kumar; Rakesh K. Arora, all of New Delhi; Neera Tiwari, Qutab Enclave; Shailendra K. Singh, New Delhi, all of Ind.

[73] Assignee: Ranbaxy Laboratories, Ltd., New Delhi, Ind.

[21] Appl. No.: 453,911

[22] Filed: May 30, 1995

[30] Foreign Application Priority Data

Apr. 22, 1994 [IN] Ind. .......................... 474/94

[51] Int. Cl.$^6$ .................................. C07D 501/04
[52] U.S. Cl. .......................... 540/215; 540/219
[58] Field of Search ..................... 540/215, 219

[56] References Cited

U.S. PATENT DOCUMENTS 3,781,282  12/1973  Garbrecht ........................ 260/243 C
3,799,924  3/1974   Jackson ........................... 260/243 C
3,925,372  12/1975  Chauvette ........................ 260/243 C

FOREIGN PATENT DOCUMENTS 1582960  1/1981  United Kingdom .

OTHER PUBLICATIONS

"Chemistry of Cephalosporin Antibiotics. XXIX 3–Halo– and 3–Methoxy–3–cephems", Journal of the American Chemical Society, 96:15, Jul. 24, 1974, pp. 4986–4987.

*Primary Examiner*—John M. Ford
*Attorney, Agent, or Firm*—Meltzer, Lippe, Goldstein, et al.

[57] ABSTRACT

A process for converting cephalosporin p-nitrobenzyl ester (Formula I) to the corresponding cephalosporin free acid (Formula II) comprising treating the cephalosporin p-nitrobenzyl ester with a metal selected from the group consisting of iron, magnesium, aluminum, and tin, and with hydrochloric acid in a mixture of water and a water-miscible organic solvent. Preferably, the metal is iron in the form of a fine powder, and the reaction is carried out at a temperature in the range of 30°–50° C.

12 Claims, No Drawings

PROCESS FOR P-NITROBENZYL ESTER CLEAVAGE IN CEPHALOSPORIN

FIELD OF THE INVENTION

The invention relates to a novel method of removing p-nitrobenzyl groups from esters of cephalosporins. More particularly, p-nitrobenzyl esters of cephalosporins are reductively cleaved with iron and hydrochloric acid in a mixture of water and organic solvent to produce the corresponding cephalosporin carboxylic acids.

BACKGROUND OF THE INVENTION p-Nitrobenzyl esters of various cephalosporins are well known stable crystalline compounds and their cleavage by Zn/HCl (U.S. Pat. No. 3,781,282), Zn/AcOH (U.S. Pat. No. 3,925,372), Zn/thiophenol (GB 1,582,960), sodium dithionite (U.S. Pat. No. 3,799,924) and Pd/C (JACS 96, 4986, 1974) have been recently described. However such methods, especially Zn/HCl for the cleavage of p-nitrobenzyl esters, result in the concomitant production of an insoluble material which complicates the isolation and recovery of the desired cephalosporin carboxylic acids. It is accordingly an objective of the present invention to provide an improved process for converting p-nitrobenzyl ester of cephalosporin to the corresponding cephalosporin carboxylic acid using Fe/HCl in high yield and quality. This novel method has not been found so far in the literature.

SUMMARY AND DETAILED DESCRIPTION OF PREFERRED EMBODIMENTS

In accordance with the present invention, a process for converting a cephalosporin p-nitrobenzyl ester represented by Formula I

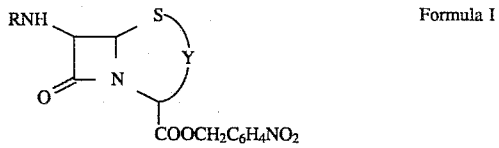

Formula I to a corresponding cephalosporin free acid represented by Formula II

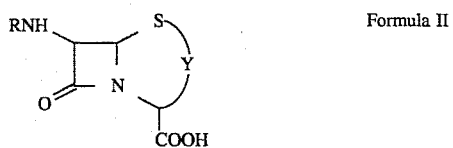

Formula II wherein R is hydrogen phenylacetyl, phenoxyacetyl or a group represented by Formula III

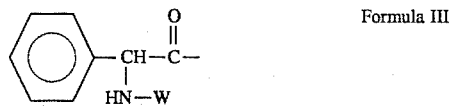

Formula III wherein W is hydrogen or t-butoxycarbonyl, and wherein Y is a group represented by Formula IV or V

Formula IV

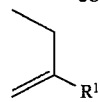

Formula V wherein $R^1$ is chloro, bromo, methyl, halomethyl, or methoxy, comprises treating the cephalosporin p-nitrobenzyl ester with a metal selected from the group consisting of iron, magnesium, aluminum, and tin, and with hydrochloric acid in a mixture of water and a water miscible organic solvent.

According to a preferred process of this invention, a cephalosporin p-nitrobenzyl ester represented by Formula I is reacted with iron and hydrochloric acid in a mixture of water and an organic solvent at a temperature between 25°–65° C., preferably at 30°–50° C., to provide the corresponding free acid represented by Formula II.

For the best results in the process, iron in the form of a fine powder is preferred and is employed in an amount between 7 to 12 moles of iron per mole of ester; however, amounts of iron in excess of this mole ratio can also be employed.

In place of iron several other metals like aluminum, magnesium, and tin can also be used this invention. However, iron metal gives the best results.

Hydrochloric acid used in the process is present in a ratio of between 3 to 10 moles per mole of cephalosporin p-nitrobenzyl ester. Preferably, the mole ratio is about 2 to 5 moles of hydrochloric acid per mole of cephalosporin p-nitrobenzyl ester.

Organic solvents which can be employed in this process are commercially available and water miscible. These solvents include alcohols, such as methanol, ethanol or isopropanol, and ethers, such as tetrahydrofuran or dioxane. The preferred solvent in the process of this invention is methanol or tetrahydrofuran.

The reduction has been carried out in a water/organic solvent mixture wherein the water comprises 10 to 40 parts by volume and the organic solvent comprises from 60 to 90 parts by volume. The preferred volume ratio of water to organic solvent is 20:80 respectively.

The invention will now be described by reference to the following specific examples.

EXAMPLE 1

7-AMINO-3-CHLORO-3-CEPHEM-4-CARBOXYLIC ACID

To a mixture of methanol (120 ml) and water (25 ml) p-nitrobenzyl 7-amino-3-chloro-3-cephem-4-carboxylate (10 gm) was added. Iron powder (10 gm) was charged at 30° C., followed by the addition of concentrated HCl (12.5 ml) in a methanol (10 ml) and water (2.5 ml) mixture over a period of 15 minutes. The reaction mixture was stirred for 1 hour. After completion of the reaction, aq. $KHCO_3$ was added to bring the pH to 8.0, followed by the addition of activated carbon. After stirring for 10 minutes, the mixture was filtered. To the filtrate was added aq. HCl to bring the pH to 4.0. The product thus separated was filtered and dried to yield 4.6 gm (80%) of 7-amino-3-chloro-3-cephem-4-carboxylic acid as a white solid. M.p. 210°–212° C.(d). IR (KBr) $cm^{-1}$: 1785,1605,1520,1330,1075,850,805,775. NMR ($D_2O$-$NaHCO_3$) δ:3.80 (dd, 2 H, S—$CH_2$), 5.20 (d, 1 H, S—CH), 5.50 (d, 1 H, N—CH).

EXAMPLE 2

7-AMINO-3-CHLORO-3-CEPHEM-4-CARBOXYLIC ACID

To a mixture of tetrahydrofuran (120 ml) and water (25 ml), p-nitrobenzyl 7-amino-3-chloro-3-cephem-4-carboxylate (10 gm) was added. Iron powder (10 gm) was charged at 30° C., followed by the addition of concentrated HCl (12.5 ml) in a tetrahydrofuran (10 ml) and water (2.5 ml) mixture over a period of 15 minutes. The reaction mixture was stirred for 1 hour. After completion of the reaction, aq. $KHCO_3$ was added to bring the pH to 8.0, followed by the addition of activated carbon. After stirring for 10 minutes, the mixture was filtered. To the filtrate was added aq. HCl to bring the pH to 4.0. The product thus separated was filtered and dried. Yield 4.17 gm (72.3%).

EXAMPLE 3

7-AMINO-3-CHLORO-3-CEPHEM-4-CARBOXYLIC ACID

To a mixture of ethanol (240 ml) and water (50 ml), p-nitrobenzyl 7-amino-3-chloro-3-cephem-4-carboxylate (20 gm) was added. Iron powder (20 gm) was charged at 30° C., followed by the addition of concentrated HCl (25 ml) in an ethanol (930 ml) and water (5.0 ml) mixture over a period of 15 minutes. The reaction mixture was stirred for 1 hour. After completion of the reaction, aq. $KHCO_3$ was added to bring the pH to 8.0, followed by the addition of activated carbon. After stirring for 10 minutes, the mixture was filtered. To the filtrate was added aq. HCl to bring the pH to 4.0. The product thus separated was filtered and dried to yield 8.42 gm (73%) of white crystalline product.

EXAMPLE 4

7-PHENOXYACETAMIDO-3-CHLORO-3-CEPHEM-4-CARBOXYLIC ACID

To a mixture of methanol (120 ml) and water (25 ml), p-nitrobenzyl 7-phenoxyacetamido-3-chloro-3-cephem-4-carboxylate (10 gm) was added. Iron powder (10 gm) was charged at 30° C., followed by the addition of concentrated HCl (25 ml) in a methanol (10 ml) and water (2.5 ml) mixture over a period of 15 minutes. The reaction mixture was stirred for 1 hour and filtered. The solvent was removed under vacuum. The residue was taken up in ethyl acetate (200 ml) and stirred with 10% aq. $KHCO_3$ soln. (100 ml). The aqueous layer was separated, treated with 5% activated carbon, filtered and the pH was adjusted to 2.00 with conc. HCl. The product thus separated was filtered and dried to yield 3.0 gm (41%) of the corresponding cephalosporanic acid. M.p. 168°–170° C. IR (KBr) $cm^{-1}$ : 3400, 1770, 1745, 1700, 1650, 1210, 750. NMR (DMSO-$d_6$) δ:3.7 (dd, 2 H, S—$CH_2$), 4.4 (s, 2 H—$OCH_2$), 4.9 (d, 1 H, S—CH), 5.5 (q, 1 H, N—CH), 6.5–7.2 (m, 5 H, Ar—H), 8.75 (d, 1 H, NH).

EXAMPLE 5

7-PHENYLACETAMIDO-3-CHLORO-3-CEPHEM-4-CARBOXYLIC ACID

The procedure described in Example 4 was repeated using p-nitrobenzyl 7-phenylacetamido-3-chloro-3-cephem-4-carboxylate as the starting material. The corresponding acid was obtained in 40.2% yield. M.p. 142°–145° C. IR (KBr) $cm^{-1}$ : 3260, 1755, 1635, 1515, 680. NMR (DMSO-$δ_6$) δ: 3.2–4.2 (m, 4 H, S—$CH_2$ & Ar—$CH_2$), 5.2 (d, 1 HS—CH), 5.7 (q, 1 H, N—CH), 7.3 (s, 5 H, Ar—H), 9.1 (d, 1 H, NH).

EXAMPLE 6

7-(D-α-t-BUTOXYCARBOXAMIDOPHENYLACETAMIDO)3-CHLORO-3-CEPHEM-4-CARBOXYLIC ACID p-Nitrobenzyl 7-(d-α-t-butoxycarboxamidophenylacetamido)-3-chloro- 3-cephem-4-carboxylate (10 gm) was suspended in a mixture of methanol (120 ml), THF (40 ml) and water (25 ml). Iron powder (10 gm) was charged at 30° C., followed by the addition of concentrated HCl (12.5 ml) in a methanol (10 ml) and water (2.5 ml) mixture over a period of 15 minutes. The reaction mixture was stirred for 1 hour and filtered. The solvent was removed and the residue was taken up in ethyl acetate (150 ml) and stirred with 10% aq. $KHCO_3$ solution (100 ml). The aqueous layer was separated and treated with 5% activated carbon, filtered and acidified to pH 2.00 with conc. HCl. The solid separated was extracted in methylene chloride and on evaporation of methylene chloride the corresponding acid 3.0 gm (38%) was obtained. M.p. 112–115(d). IR (KBr) $cm^{-1}$ : 3330, 2925, 1785, 1700, 1365, 1160, 690. NMR ($CDCl_3$) δ:1.35 (s, 9 H, $CH_3$), 3.9 (q, 2 H,S—$CH_2$), 4.7 (d, 1 H, S—CH), 5.3–6.1 (m, 2 H, Ar—CH & N—CH), 7.0 (s, 5 H, Ar—H).

EXAMPLE 7

7-PHENOXYACETAMIDO-3-CHLORO-3-CEPHEM-4-CARBOXYLIC ACID p-Nitrobenzyl 7-phenoxyacetamino-3-methylene-3-cephem- 4-carboxylate-1-oxide (10 gm) was suspended in a mixture of methanol (120 ml), THF (40 ml) and water (25 ml). Iron powder (10 gm) was charged at 30° C., followed by the addition of concentrated HCl (12.5 ml) in a methanol (10 ml) and water (2.5 ml) mixture over a period of 15 minutes. The reaction mixture was stirred for 1 hour. The reaction mixture was filtered to remove unreacted iron. The solvent was evaporated under vacuum and to the residue, ethyl acetate was added. The solid thus separated was filtered, washed with ethyl acetate and dried to yield 2.1 gm (30%) of the corresponding cephalosporanic acid. M.p. 192°–194° C. IR (KBr) $cm^{-1}$ : 3540, 3350, 1775, 1670, 1595, 1435, 1280, 1245, 1160, 1100, 1015, 915, 855, 745. NMR (DMSO-$d_6$) δ: 3.7 (dd, 2 H, S—$CH_2$), 4.5 (d, 2 H, —$OCH_2$), 4.7–5.5 (m, 4 H, exomethylene, N—CH & S—CH) , 5.6 (q, 1 H, HN—CH), 6.5 (m, 5 H, Ar—H) , 7.9 (d, 1 H, NH).

EXAMPLE 8

7-PHENLYACETAMIDO-3-CHLORO-3-CEPHEM-4-CARBOXYLIC ACID-1-OXIDE

Using the procedure described in Example 7, p-nitrobenzyl 7-phenlyacetamido-3-chloro-3-cephem-4-carboxylate-1-oxide was reacted with iron and HCl to obtain the corresponding acid in 28.4% yield. M.p. 185°–191° C. IR (KBr) $cm^{-1}$ : 3300, 1770, 1720, 1660, 1510, 1200, 1000, 720 NMR (DMSO-$d_6$) δ: 3.4 (d, 2 H,S—$CH_2$), 3.6 (d,2 H,Ar—$CH_2$), 4.7–5.4 (m, 5 H, N—CH, exomethylene ($CH_2$), S—CH & HOOC—CH), 6.9 (s, 5 H, Ar—H), 7.6 (d, 1 H,NH)

EXAMPLE 9

7-AMINO-3-METHYL-3-CEPHEM-4-CARBOXYLIC ACID

To a mixture of ethanol (120 ml) and water (25 ml), p-nitrobenzyl 7-amino-3-methyl-3-cephem-4-carboxylate (10 gm) was added. Iron powder (10 gm) was charged at 30° C., followed by the addition of concentrated HCl (12.5 ml) in a methanol (10 ml) and water (2.5 ml) mixture over a period of 15 minutes. The reaction mixture was stirred for 1 hour. After completion of the reaction, aq. $KHCO_3$ was added to bring the pH to 8.0, followed by the addition of activated carbon. After stirring 10 minutes, the mixture was filtered. To the filtrate was added aq. HCl to bring the pH to 4.0. The product thus separated was filtered and dried to yield 4.3 gm (70.3%) of 7-amino-3-methyl-3-cephem-4-carboxylic acid as a white solid product. M.p. 217°–219° C.(d). IR(KBr) $cm^{-1}$ 3150, 1800, 1650, 1625, 1525, 1420, 1350, 790. NMR ($D_2O$-DCl) δ:2.1 (s, 3 H,—$CH_3$), 5.41(d, 1 H, S—CH), 5.86(m, 1 H, N—CH).

EXAMPLE 10

7-AMINO-3-CHLORO-3-CEPHEM-4-CARBOXYLIC ACID p-Nitrobenzyl 7-amino-3-chloro-3-cephem-4-carboxylate (10 gm) was suspended in a mixture of methanol (120 ml) and water (25 ml). Aluminum powder (10 gm) was charged at 30° C., followed by the addition of concentrated HCl (12.5 ml) in a methanol (10 ml) and water (2.5 ml) mixture over a period of 15 minutes. The reaction mixture was stirred for 1 hour. After completion of the reaction, aq. $KHCO_3$ was added to bring the pH to 8.0 followed by the addition of activated carbon. After stirring for 10 minutes, the reaction mixture was filtered. To the filtrate was added aq. HCl to bring the pH to 4.0. The product thus separated was filtered and dried. Yield: 3.9 gm (68%).

EXAMPLE 11

7-AMINO-3-CHLORO-3-CEPHEM-4-CARBOXYLIC ACID p-Nitrobenzyl 7-amino-3-chloro-3-cephem-4-carboxylate (10 gm) was suspended in a mixture of methanol (120 ml) and water (25 ml). Tin powder was charged at 30° C., followed by the addition of concentrated HCl (25 ml) in a methanol (20 ml) and water (5 ml) mixture over a period of 15 minutes. The reaction mixture was stirred for 1 hour. After completion of the reaction, aq. $KHCO_3$ was added to bring the pH to 8.0, followed by the addition of activated carbon. After stirring for 10 minutes, the mixture was filtered. To the filtrate was added aq. HCl to bring the pH to 4.0. The product thus separated was filtered and dried. Yield: 3.9 g (68%).

While the invention has been described by reference to specific embodiments, this was for purposes of illustration only. Numerous alternative embodiments will be readily apparent to those skilled in the art and are considered to be within the scope of the invention.

We claim:

1. A process for converting a cephalosporin p-nitrobenzyl ester represented by Formula I

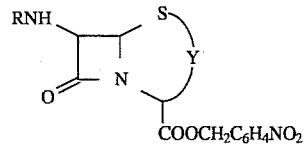

Formula I to a corresponding cephalosporin free acid represented by Formula II

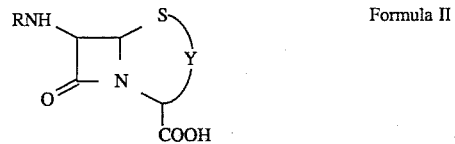

Formula II wherein R is hydrogen, phenylacetyl, phenoxyacetyl or a group represented by Formula III

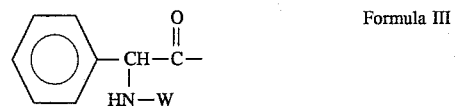

Formula III wherein W is hydrogen or t-butoxycarbonyl, and wherein Y is a group represented by Formula IV or V

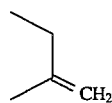

Formula IV

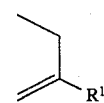

Formula V wherein $R^1$ is chloro, bromo, methyl, halomethyl, or methoxy, comprising treating the cephalosporin p-nitrobenzyl ester with a metal selected from the group consisting of iron, magnesium, aluminum, and tin, and with hydrochloric acid in a mixture of water and a water miscible organic solvent.

2. The process of claim 1 wherein the treatment is carried out at a temperature in the range of 25°–65° C.

3. The process of claim 1 wherein the treatment is carried out at a temperature in the range of 30°–50° C.

4. The process of claim 1 wherein the amount of hydrochloric acid is in the range of 3–10 moles per mole of said p-nitrobenzyl cephalosporin ester.

5. The process of claim 1 wherein the amount of hydrochloric acid is in the range of 2–5 moles per mole of said p-nitrobenzyl cephalosporin ester.

6. The process of claim 1 wherein the amount of said metal is in the range of 7–12 moles per mole of said p-nitrobenzyl cephalosporin ester.

7. The process of claim 1 wherein the amount of said metal is in the range of 8–10 moles per mole of said p-nitrobenzyl cephalosporin ester.

8. The process of claim 1 wherein said organic solvent is an alcohol, an ether, or a combination thereof.

9. The process of claim 8 wherein said alcohol is methanol, ethanol, or isopropanol.

10. The process of claim 8 wherein said ether is tetrahydrofuran or dioxane.

11. The process of claim 1 wherein said metal is iron.

12. The process of claim 11 wherein said iron is in the form of a fine powder

* * * * *